United States Patent [19]

Robinson et al.

[11] 4,379,896

[45] Apr. 12, 1983

[54] KETO/POLYCARBOXY CONTAINING RESIN

[75] Inventors: Joseph G. Robinson, Winchcombe; David I. Barnes, Cheltenham; Angela M. Carswell, Longhope, all of England

[73] Assignee: Coal Industry (Patents) Limited, England

[21] Appl. No.: 333,886

[22] Filed: Dec. 23, 1981

Related U.S. Application Data

[62] Division of Ser. No. 174,152, Jul. 31, 1980, Pat. No. 4,346,212.

[30] Foreign Application Priority Data

Sep. 21, 1979 [GB] United Kingdom ............... 7932778

[51] Int. Cl.$^3$ .............................................. C08G 2/30
[52] U.S. Cl. ..................... 525/472; 528/220; 528/229; 528/233; 528/247
[58] Field of Search ............... 528/247, 220, 229, 233; 525/472

[56] References Cited

U.S. PATENT DOCUMENTS 3,078,279  2/1963  McCracken et al. ............ 260/346.3
4,173,573  11/1979  Schulz et al. .................... 260/346.4

FOREIGN PATENT DOCUMENTS 633923 12/1949 United Kingdom .

OTHER PUBLICATIONS

English Language Translation of German Document Number 420,442.
Chemical Abstracts, vol. 76, (1972), No. 46746v, pp. 18–19.

*Primary Examiner*—Harold D. Anderson
*Attorney, Agent, or Firm*—Stevens, Davis, Miller & Mosher

[57] ABSTRACT

This invention relates to thermally stable resins and provides such a resin made from cheaply available coal-derived materials, whereas presently available resins are made from increasingly expensive oil-derived materials.

The resin comprises the condensation product of a reaction between an aromatic diamine and a phenanthrene-formaldehyde reaction product, which product has been oxidized to produce keto groups bridging the phenanthrene moieties and carboxy groups. The condensation product is a poly-(amine-imide).

The invention also includes a method of making the resin and varnishes containing the resin.

The resin will find use for instance as a high temperature insulator or in glass or asbestos laminates in compressor blades.

1 Claim, 14 Drawing Figures

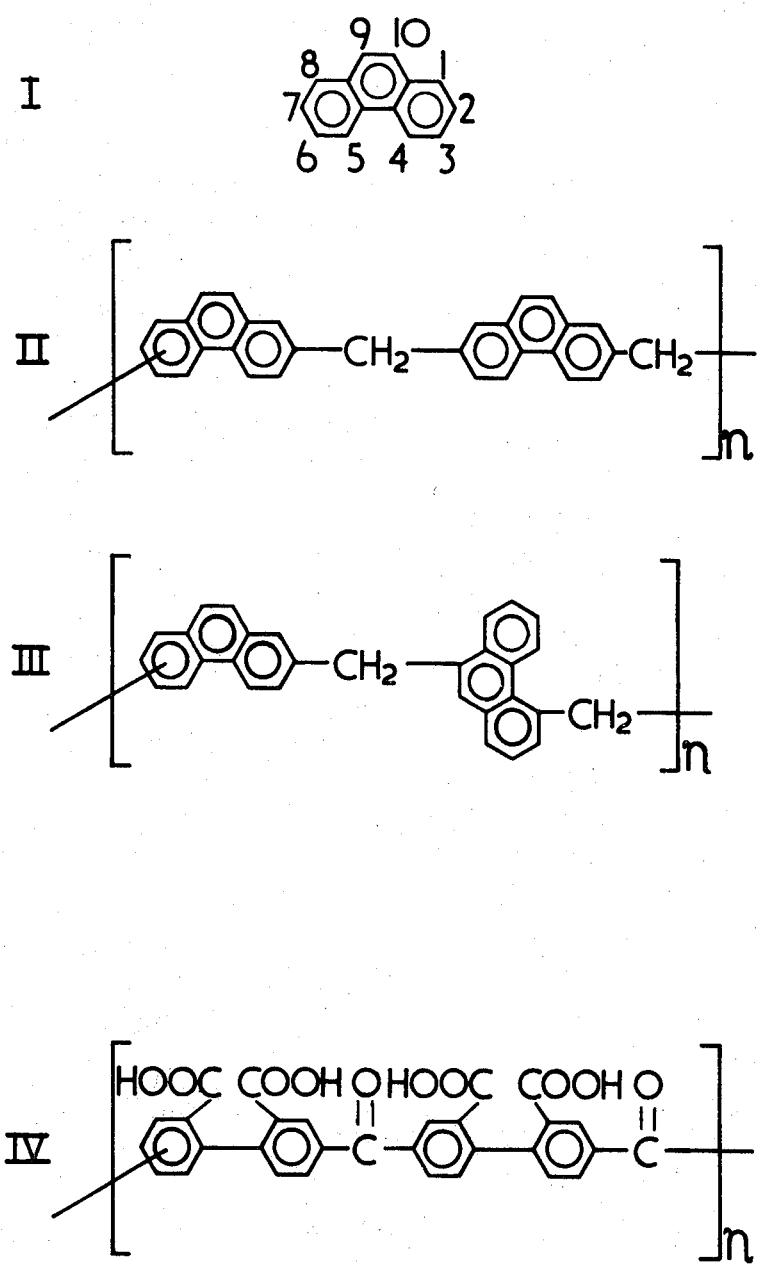

V 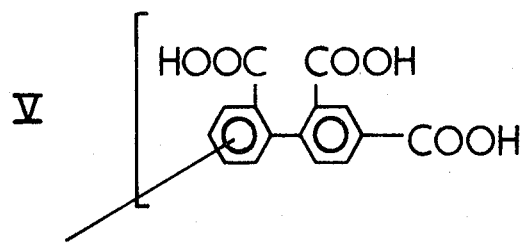
VI 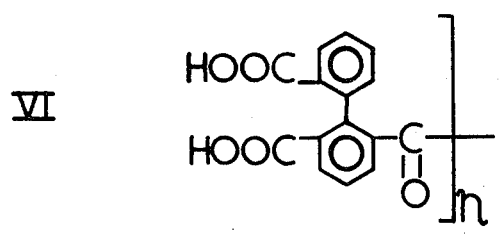
VII 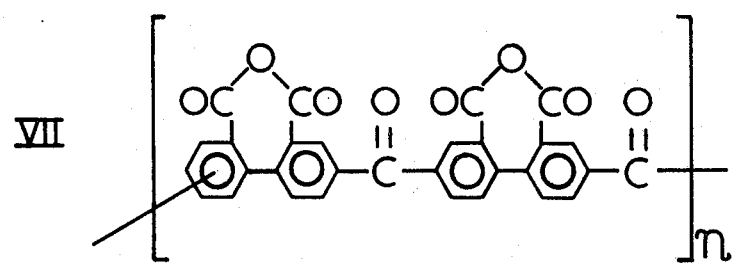
VIII 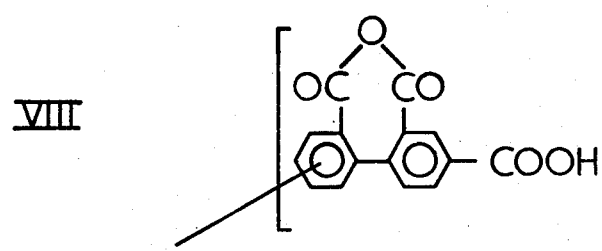

IX 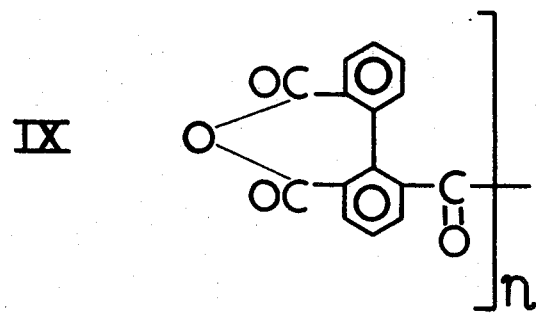
X 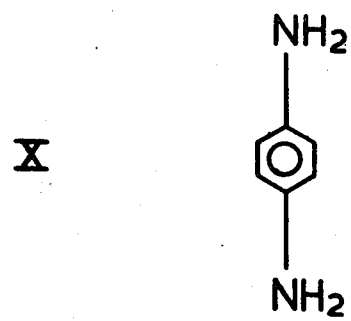

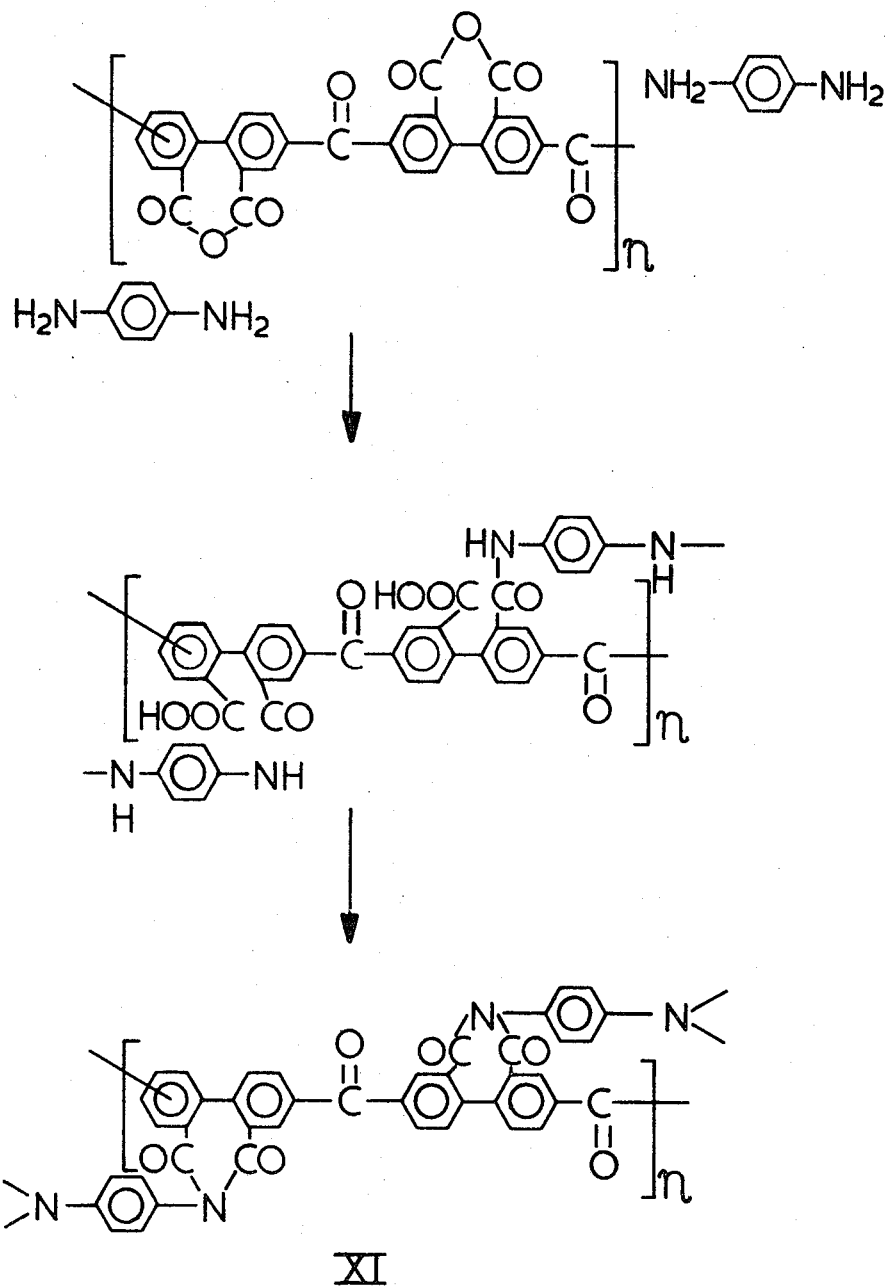

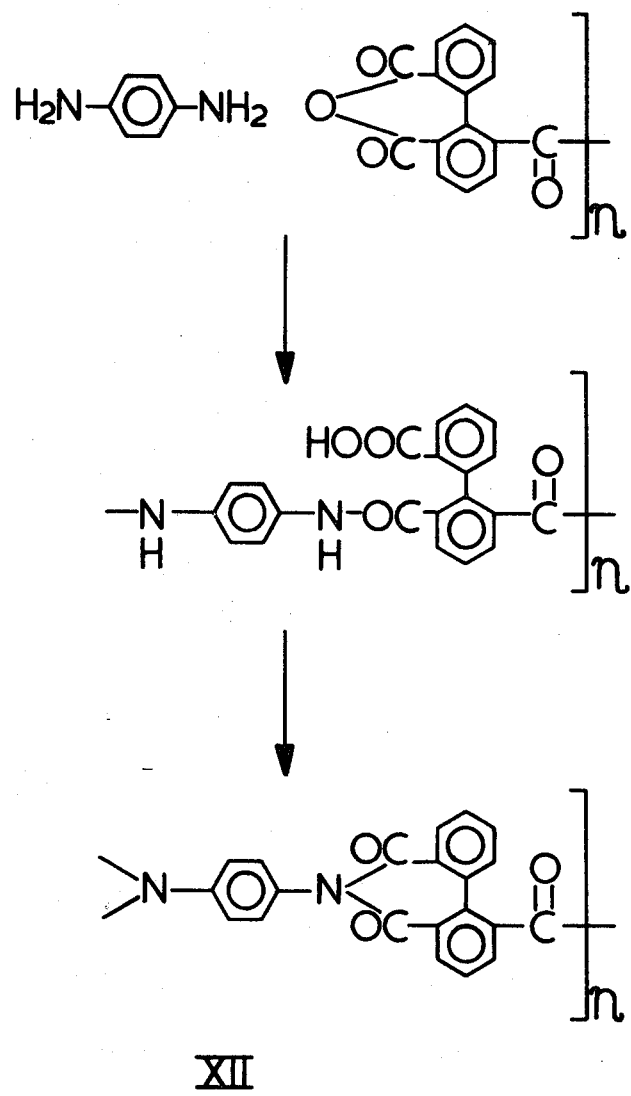
XII

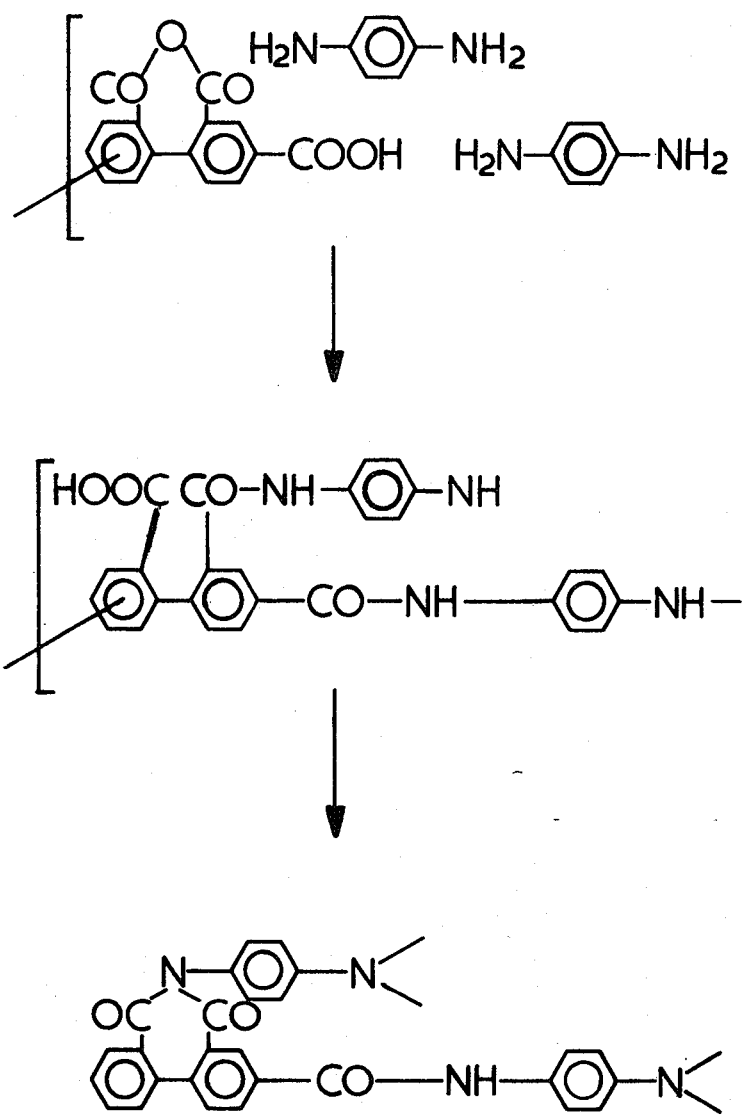

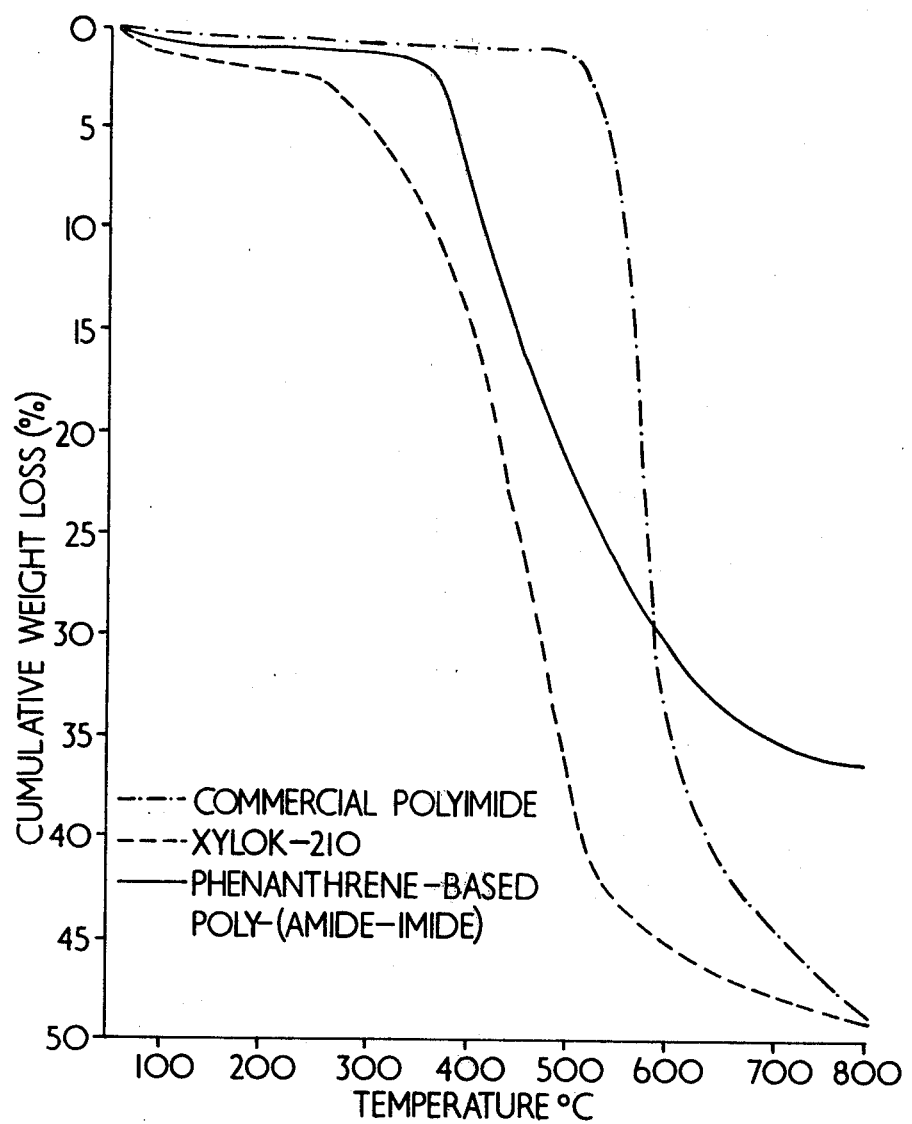

KETO/POLYCARBOXY CONTAINING RESIN

This is a division of application Ser. No. 174,152 filed July 31, 1980 now U.S. Pat. No. 4,346,212.

This invention relates to a novel poly-(amide-imide) resin, a process for its perparation and its use as a temperature resistant resin. In particular, but not exclusively, the invention relates to such a resin produced from cheaply available materials.

Several resins have been developed which are stable at high temperatures (in the region from 200° to 250° C. and even higher) and which retain their mechanical properties at these temperatures. These resins include polyimides, poly-(amide-imides), polybenzimidazoles, and polyphenylenes. These resins are derived from expensive materials and are difficult to make. They have limited commercial acceptability either because of their high cost or because their chemical or physical properties are not adequate for their intended use. There are also resins made by Friedel-Crafts-type reactions which are cheaper but are less thermally stable than those mentioned above.

Another disadvantage of presently known resins is that they are made from petrochemicals. As the supply of petrochemicals is limited and rapidly decreasing, the cost of these resins will go up, and eventually it will not be possible to produce them economically.

There is a need for a thermally stable resin which is relatively cheap, which is made from readily available materials and which has good mechanical and physical properties. The resin would find use as a lamp capping cement, as a high temperature insulator, in copper clad high temperature printed circuits, in electric heater panels, in transformers and in glass or asbestos laminates for use as compressor blades.

According to a first aspect of the present invention, there is provided a method of producing a phenanthrene-derived poly-(amide-imide) resin comprising the steps of
1. reacting a phenanthrene with formaldehyde or a formaldehyde donor in the presence of an acid catalyst to give a phenanthrene-formaldehyde reaction product having substantially only methylene bridges;
2. oxidising the reaction product to oxidise the methylene bridges to keto groups and to break the 9, 10 bond in the phenanthrene moieties to produce a polycarboxylated reaction product; and
3. reacting the polycarboxylated reaction product with an aromatic diamine to produce a poly-(amide-imide) resin.

The phenanthrene may be pure, or may contain alkylated derivatives. Phenanthrene in a pure enough state may be readily obtained from the anthracene oil fraction of coal tar, which is produced during the coking or liquid extraction of coal. This feedstock will remain in plentiful supply for as long as coal stocks last.

The formaldehyde may be supplied as formaldehyde itself, as formalin (38% formaldehyde in water), or, preferably, as paraform, a solid polymer of formaldehyde and water containing about 87% formaldehyde.

The acid catalyst may be protonic, such as hydrochloric acid, or a Lewis acid, such as aluminium chloride, and is preferably sulphuric acid, advantageously having a concentration of 50% in water.

To ensure that substantially only methylene bridges are obtained, it is preferred that the molar ratio of phenanthrene to formaldehyde is about 1 to 1 and that of phenanthrene to acid catalyst is about 1 to 2.

Preferably, the reaction of phenanthrene with formaldehyde is carried out in glacial acetic acid as the solvent. The glacial acetic does not dissolve the reaction product which therefore appears as an easily collectable precipitate.

Preferably, the reaction product is oxidised by use of a peroxy organic acid, such as peroxy-acetic acid. Conveniently, the oxidation is carried out in an ether-like solvent such as dimethoxyethane.

The polycarboxylated reaction product contains many adjacent carboxyl groups (see later) and it is desirable that some, at least, of the adjacent carboxyl groups are dehydrated to form acid anhydrides, for instance by treatment with acetic anhydride.

The polycarboxylated resin or its dehydrated derivative is then reacted wth an aromatic diamine, such as 1,4 diamino benzene. Since there will be in the polycarboxylated reaction product some carboxyl groups that are not adjacent other carboxyl groups and which therefore cannot be converted into anhydrides, the final product will contain both amide and imide linkages and will thus be a poly-(amide-imide) resin.

It is thought that the following reaction scheme indicates the method by which the poly-(amide-imide) resin is formed, although the invention is not to be construed as being limited by the explanation.

Phenanthrene (I) when reacted with formaldehyde in the presence of an acid catalyst forms linkages from any one of the 10 positions on the phenanthrene nucleus. The linkages may be either methylene (—CH$_2$—) or ether (—CH$_2$—O—CH$_2$—) groups. However because ether groups are not of adequate thermal stability the reaction conditions should be chosen to prevent any substantial formation of these linkages. In the reaction product there will be from 2 to 5 phenanthrene moieties per molecule, linked mainly by methylene bridges. There will be two different types of linkage. In the first type only the 1 to 8 positions are involved. In the second type the 9 or 10 position is involved. These two types of linkage are exemplified by II and III respectively.

On oxidation of the type of molecules exemplified by II, the 9, 10 bonds of the phenanthrene moieties are broken, the 9 and 10 carbon atoms are oxidised to carboxyl groups, and the methylene bridges are oxidised to keto groups, to give a molecule as shown in IV.

The presence of the keto groups is beneficial to the stability of the molecule because it deactivates the aromatic nuclei to attack by oxidising agents, which are electrophilic.

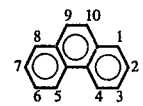  I

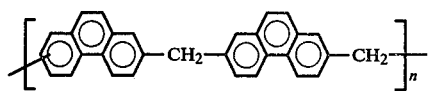  II

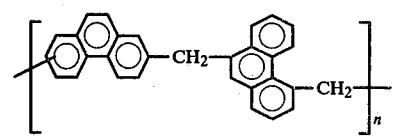  III

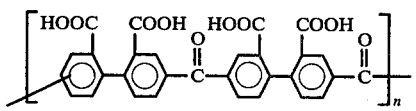 IV

On oxidation of the type of molecules exemplified by III, the 9, 10 bond of the phenanthrene moieties are broken and the 9 and 10 carbon atoms are oxidized to carboxyl groups. The bond between a phenanthrene moiety and any methylene group attached to its 9 and 10 position is broken, thereby leaving the methylene group susceptible to complete oxidation. These methylene groups, which may still be attached to another phenanthrene moiety, are oxidized to carboxyl groups. The oxidation thus gives rise to two molecules as shown at V and VI.

On treatment with an acid anhydride, the adjacent carboxyl groups of compounds such as IV, V and VI are dehydrated to give acid anhydrides such as VII, VIII and IX.

The acid anhydrides are then treated with a diamine, such as 1, 4 diamino benzene (X). Compounds of the type VII and IX probably react in two stages as shown in schemes XI and XII. In the first stage amide linkages are formed. This occurs at room temperature. In the second stage, which occurs on heating at temperatures up to about 300° C., imide linkages are formed. However, compounds of the type VIII react with the diamine as shown in scheme XIII, where there is shown the formation of both imide and amide linkages.

The presence of the amide linkage reduces to some extent the stability of the resin since they are more susceptible to oxidation at elevated temperature than are imide linkages. The most predominant type of linkages formed in the acid catalysed reaction of formaldehyde and phenanthrene are those involving the 1 to 8 positions. Since there are fewer linkages involving the 9 or 10 positions, there are fewer amide than imide linkages in the final resin. However, the thermal stability of the resin would be significantly improved by the elimination of all amide linkages therein.

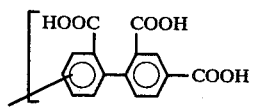 V

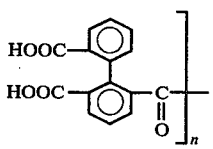 VI

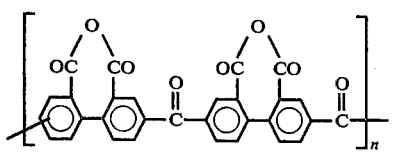 VII

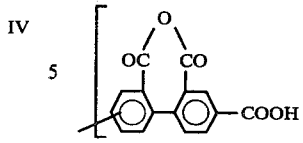 VIII

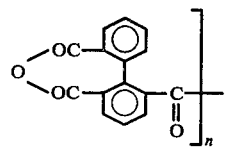 IX

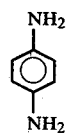 X

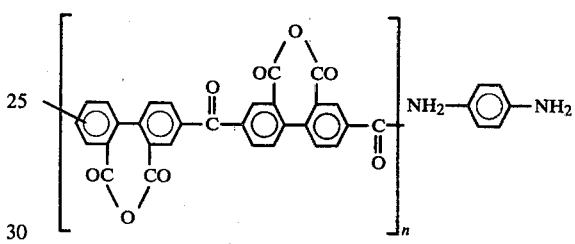

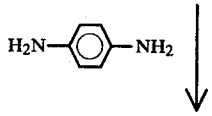

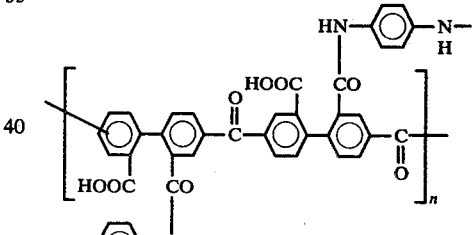

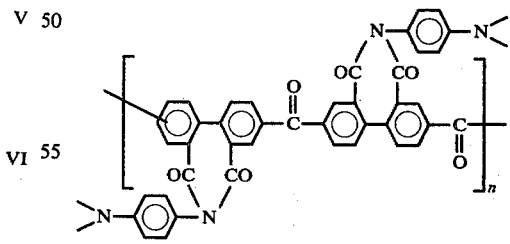 XI

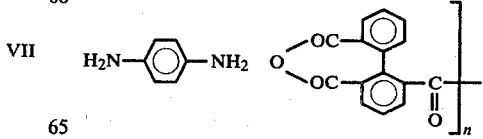

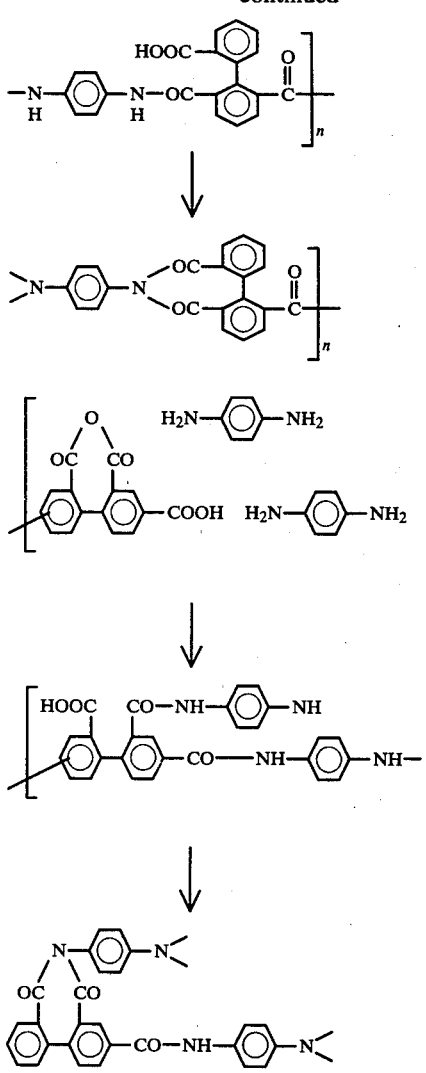

According to a second aspect of the present invention, there is provided a poly-(amide-imide) resin comprising the condensation product of a reaction between an aromatic diamine and an acid-catalysed phenanthrene-formaldehyde reaction product which has been oxidised to produce keto groups bridging the phenanthrene moieties and carboxyl groups.

According to a third aspect of the present invention, there is provided an intermediate in the formation of a poly-(amide-imide) resin comprising an acid-catalysed phenanthrene-formaldehyde reaction product which has been oxidised to produce keto groups bridging the phenanthrene moieties and carboxylate groups.

The poly-(amide-imide) resin will find use in any of the fields previously mentioned in this specification. The present invention also includes poly-(amide-imide) resins when made according to the first aspect of the invention and varnishes including poly-(amide-imide) resins according to the invention.

The invention will now be described by way of example only, with reference to the accompanying drawing, which shows a graph illustrating the thermal stability of various resins as determined by thermogravimetric analysis.

A poly-(amide-imide) resin was prepared as follows:

A solution of phenanthrene (178.2 g 1.0 M) in a mixture of glacial acetic acid (1000 g), sulphuric acid (98% 200 g, 2.0 M) and water (32.0 g) was heated to a temperature of 100° C. A solution of formaldehyde (38%, 78.9 g, 1.0 M) was run into the phenanthrene solution over a period of 4 hours, during which time the mixture was vigorously stirred. At the end of the 4 hour period the mixture was filtered and the resin was extracted with chloroform (3×200 ml). The resulting solution was washed with distilled water until neutral and the chloroform removed by distillation in a rotary evaporator at 50° C. and 20 mm Hg, to yield a dark brown reaction product. Analysis of the product by proton nuclear magnetic resonance spectrometry, elemental analysis and gel permeation chromatography showed that the product contained predominantly species containing 2, 3 or 4 phenanthrene moieties linked by methylene groups. The yield of the product was 180 g.

The reaction product (150 g) was dissolved in dimethoxyethane (650 g) and was treated with peracetic acid (1500 g), which was added over a period of 2 hours. The reaction mixture was maintained under slight reflux at a temperature of 85° C. After a further 2 hours the reaction mixture was diluted with water (4,000 ml), and the pH of the mixture was raised to 9 by addition of sodium hydroxide solution. The solution was filtered and acidified with concentrated hydrochloric acid to produce a precipitate which was collected and dried at a temperature of 60° C. The yield of the oxidised product was 136 g.

The oxidised product (63 g) was stirred with a mixture of glacial acetic acid (300 g) and acetic anhydride (140 g) for 3 hours at 120° C. The reaction mixture was filtered and the precipitate was washed with ice cold water and dried at 60° C. for 3 hours, to produce an anhydride product.

The anhydride product (24 g) was dissolved in dimethyl sulphoxide (100 ml) and was added with stirring to a solution of 1,4 diamino benzene (10.81 g) in dimethyl sulphoxide (50 ml) to produce the amide linkages. The resulting solution was poured onto a clear glass plate and heated in an oven for 3 hours, the temperature gradually being raised to a maximum of 300° C. at which it was maintained for the last hour. This produced a poly-(amide-imide) resin as a dark thin film.

Proton magnetic resonance spectrometry and infra red spectrometry indicated the presence of both amide and imide linkages in the final resin.

The poly- (amide-imide) resin was subjected to thermogravimetric analysis in a nitrogen atmosphere. A commercial Friedel Crafts resin ("Xylok"-210) and a commercial poly-imide resin ("Kapton") were also subjected to thermogravimetric analysis in a nitrogen atmosphere. The results of the analysis are shown in the drawing. It can been seen from this that the poly-(amide-imide) resin is less thermally stable than "Kapton" but more thermally stable than the "Xylok"-210. It begins to decompose in the region of 350°–400° C. as compared to 500°–550° C. for "Kapton" and 250°–300° C. for "Xylok"-210.

It is therefore clear that the poly- (amide-imide) will be useful as a heat resistant resin, and will be of commercial significance because it can be made by a simple process from cheaply available coal derived materials.

"Kapton" and "Xylok"-210 are registered trade marks.

We claim:

1. A keto/polycarboxyl containing resin comprising an acid-catalysed phenanthrene-formaldehyde reaction product which has been oxidised to produce keto groups bridging the phenanthrene moieties and carboxyl groups.

* * * * *